United States Patent [19]
Walther et al.

[11] 3,975,368
[45] Aug. 17, 1976

[54] PHARMACEUTICAL COMPOSITIONS CONTAINING AN N-(FURYL- OR THIENYL-METHYL)-DESOXY-NORMORPHINE OR NORCODEINE AND METHOD OF USE

[75] Inventors: Gerhard Walther; Herbert Merz; Adolf Langbein; Klaus Stockhaus, all of Ingelheim am Rhein, Germany

[73] Assignee: Boehringer Ingelheim GmbH, Ingelheim am Rhein, Germany

[22] Filed: Oct. 8, 1975

[21] Appl. No.: 620,847

Related U.S. Application Data

[62] Division of Ser. No. 396,171, Sept. 11, 1973, Pat. No. 3,928,359.

[30] Foreign Application Priority Data

Sept. 14, 1972  Germany............................ 2245141

[52] U.S. Cl. ............................................... 424/260
[51] Int. Cl.² ........................................ A61K 31/485
[58] Field of Search .................................... 424/260

[56] References Cited
UNITED STATES PATENTS 3,793,329  2/1974  Merz et al............................ 424/260
3,923,987  12/1975  Merz et al............................ 424/260

FOREIGN PATENTS OR APPLICATIONS 143,107  3/1948  Australia............................ 260/285
843,752  8/1960  United Kingdom................. 260/285

*Primary Examiner*—Norman A. Drezin
*Attorney, Agent, or Firm*—Hammond & Littell

[57] ABSTRACT

Pharmaceutical compositions containing as an active ingredient a compound of the formula

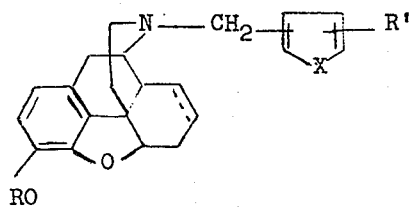

wherein
R is hydrogen, methyl or acetyl,
R' is hydrogen or methyl, and
X is oxygen or sulfur,
or a non-toxic, pharmacologically acceptable acid addition salt thereof; and a method of using the same as opiate antagonists, analgesics and antitussives.

12 Claims, No Drawings

PHARMACEUTICAL COMPOSITIONS CONTAINING AN N-(FURYL- OR THIENYL-METHYL)-DESOXY-NORMORPHINE OR NORCODEINE AND METHOD OF USE

This is a division of copending application Ser. No. 396,171 filed Sept. 11, 1973 now U.S. Pat. No. 3,928,359.

This invention relates to novel pharmaceutical compositions containing as an active ingredient an N-(furyl-or thienyl-methyl)-Δ7-desoxy-normorphine or norcodeine or a corresponding dihydro-compound or a non-toxic acid addition salt thereof, as well as to a method of using the same as opiate antagonists, analgesics and antitussives.

More particularly, the present invention relates to novel pharmaceutical compositions containing as an active ingredient a compound of the formula

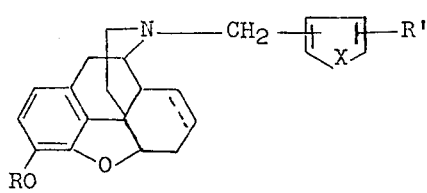

(I)

wherein
R is hydrogen, methyl or acetyl,
R' is hydrogen or methyl, and
X is oxygen or sulfur,
or a non-toxic, pharmacologically acceptable acid addition salt thereof.

A preferred sub-genus thereunder is constituted by compositions containing a compound of the formula I, where R is hydrogen and the other variables have the meanings previously defined, or a non-toxic acid addition salt thereof.

The compounds embraced by formula I may be prepared by a number of different methods among which the following have proved to be especially convenient and efficient:

Method A

By alkylating a nordesomorphine or nordesocodeine of the formula

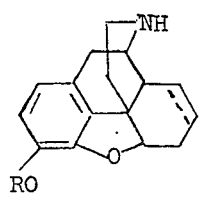

(II)

wherein R has the same meanings as in formula I, with a heteroarylmethyl derivative of the formula

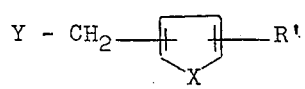

(III)

wherein
R' and X have the meanings previously defined, and
Y is halogen, preferably chlorine, bromine or iodine, alkyl $-SO_2-O-$ or aryl$-SO_2-O-$.

The reaction of the nor-compound of the formula II is performed with the calculated amount, or a slight excess thereover, of the heteroarylmethyl derivative of the formula III, advantageously in the presence of an acid-binding agent. Examples of suitable acid-binding agents are tertiary amines, such as triethylamine or N,N-dicyclohexyl-ethylamine; alkali metal carbonates, such as sodium carbonate or potassium carbonate; alkali metal bicarbonates, preferably sodium bicarbonate; or alkali metal hydroxides or oxides. The reaction is advantageously carried out in an inert organic solvent medium, such as tetrahydrofuran, dioxane, methylene chloride, dimethylformamide, dimethylsulfoxide or a mixture of two or more of these, preferably mixtures of tetrahydrofuran and dimethylformamide. The reaction temperature may vary within wide limits, but a temperature between 0°C and the boiling point of the particular solvent medium which is used is preferred. After completion of the reaction, the reaction product is isolated by conventional methods.

Method B

By reducing a carbonamide or thioamide of the formula

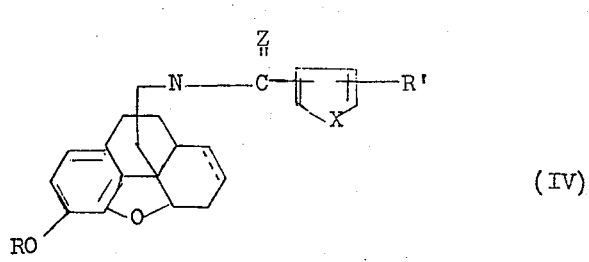

(IV)

wherein
R, R' and X have the same meanings as in formula I, and
Z is oxygen or sulfur.

The reduction of a carbonamide of the formula IV (Z = Oxygen) may be effected by various known methods; among these, the reduction with a complex hydride, in particular with lithium aluminum hydride is preferably used. Either the calculated quantity or, preferably, an excess of the complex hydride, advantageously up to double the calculated quantity, is provided. The reduction is advantageously performed in a suitable inert solvent such as diethylether, diisopropylether or, most preferably, tetrahydrofuran. The reaction temperature is variable within wide limits. Temperatures between 0°C and the boiling point of the solvent are preferred.

If R in formula IV is acetyl, the O-acetyl group is split off simultaneously with the reduction of the carbonyl group, and in this case a compound of the formula I is obtained wherein R is hydrogen.

Methods for reducing a thioamide of the formula IV (Z = sulfur) are also well known. The reduction may be effected with the aid of a complex hydride, such as lithium aluminium hydride; or with nascent hydrogen generated in situ by Zn/acetic acid or aluminum amalgam/water, for example; or with catalytically activated hydrogen, in the presence of Raney nickel, for instance; or also electrochemically.

In all instances the reduction product is isolated, purified and crystallized by conventional methods.

Method C

For the preparation of a compound of the formula I wherein X is oxygen, by subjecting a nor-compound of the formula II or an acid addition salt thereof to a Mannich reaction with a furan of the formula

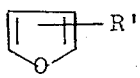 (V)

wherein R' has the same meanings as in formula I, in the presence of formaldehyde.

The reaction is carried out in weakly acid solution, especially in acetic acid solution in a suitable solvent, such as water, lower alkanols, tetrahydrofuran, dioxane or mixtures of any two or more of these. The furan of the formula V is provided in the stoichiometric amount or in slight excess thereover, either dissolved or suspended in the solvent medium. The formaldehyde may be provided in the form of paraformaldehyde or preferably in the form of an aqueous solution in the calculated amount or in excess thereover. The reaction temperature may vary between 0°C and the boiling point of the particular solvent medium which is employed, but the preferred temperature range is from 20° to 40°C. After completion of the reaction, the reaction product is isolated and crystallized by conventional methods.

Method D

For the preparation of a compound of the formula I wherein R is hydrogen, by subjecting a compound of the formula

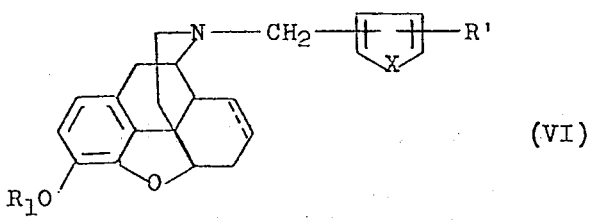 (VI)

wherein
  R' and X have the same meanings as in formula I, and
  $R_1$ is acyl, such as formyl, acetyl, propionyl, benzoyl, furoyl or thenoyl; lower alkyl, aralkyl, such as benzyl; or methoxymethyl,
to an ether or ester cleavage reaction.

The ester cleavage may be effected by hydrolysis in an alkaline or acid medium, for example; an acyl group may, however, also be removed by reduction with a complex hydride, such as lithium aluminum hydride, for instance.

The ether cleavage is effected by hydrolysis with a mineral acid, preferably hydrogen bromide or hydrogen iodide; or with a Lewis-acid, such as aluminum chloride or boron bromide; or also with pyridine hydrochloride. It is also possible to effect the ether cleavage in an alkaline medium, such as with sodium hydroxide or potassium hydroxide in diethyleneglycol.

The ester or ether cleavage product is isolated, purified and crystallized by conventional methods.

Method E

For the preparation of a compound of the formula I wherein R is methyl or acetyl, by methylating or acetylating a compound of the formula I wherein R is hydrogen.

The acetylation is effected by reaction with an activated acetic acid derivative, such as an acetyl halide, especially acetyl chloride, or acetic acid anhydride.

The methylation is effected with conventional methylating agents, such as dimethylsulfate, methyl iodide or diazomethane.

In either case, the reaction product is isolated, purified and crystallized by conventional methods.

Method F

By subjecting a compound of the formula II to a Leuckart-Wallach reaction with an aldehyde of the formula

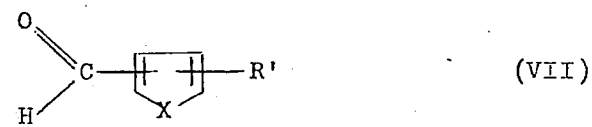 (VII)

wherein R' and X have the same meanings as in formula I, in the presence of formic acid.

The reaction is preferably carried out in aqueous solution, but it may also be performed in a suitable organic solvent or also by melting the reactants without a solvent medium. The aldehyde of the formula VII is provided in the stoichiometric amount or in excess thereover, preferably in a ratio of 1.5 to 2 mols of aldehyde per mol of nor-compound of the formula II. The formic acid is advantageously provided in excess, preferably up to 10 mols per mol of nor-compound. The reaction temperature range is from 50° to 200°C, preferably 80° to 150°C.

The reaction product is isolated, purified and crystallized by conventional methods.

The starting compounds required for methods A to F are, to a large extent, known compounds or may be prepared by known methods.

For instance, compounds of the formula II may be obtained by tosylation of codeine and subsequent reduction with lithium aluminum hydride to form Δ7-desoxy-codeine. De-methylation of the latter by bromocyanogen degradation, for example, yields Δ7-desoxy-norcodeine which, in turn, can be converted by hydrogenation of the double bond into the corresponding dihydro-desoxy-norcodeine. The corresponding normorphine derivatives are obtained by ether cleavage of Δ7-desoxy-norcodeine or dihydro-desoxy-norcodeine.

The compounds embraced by formulas III, V and VII are described in the literature.

A compound of the formula IV may be obtained by acylation of a compound of the formula II with a corresponding heteroaryl-carboxylic acid or -thiocarboxylic acid derivative. A thioamide of the formula IV may also be prepared by thionation with phosphorus pentachloride, for instance, of a corresponding carbonamide.

A compound of the formula VI may be obtained by acylation or alkylation or aralkylation of a compound of the formula I wherein R is hydrogen.

The compounds of the formula I are bases and therfore form acid addition salts with inorganic or organic acids. Examples of non-toxic, pharmacologically acceptable acid addition salts are those formed with hydrochloric acid, hydrobromic acid, hydroiodic acid, hydrofluoric acid, sulfuric acid, phosphoric acid, nitric acid, acetic acid, propionic acid, butyric acid, valeric acid, pivalic acid, caproic acid, oxalic acid, malonic acid, succinic acid, maleic acid, fumaric acid, lactic acid, tartaric acid, citric acid, malic acid, benzoic acid, phthalic acid, cinnamic acid, salicylic acid, ascorbic acid, 8-chlorotheophylline, methanesulfonic acid, ethanephosphonic acid or the like.

The following examples further illustrate the present invention and will enable others skilled in the art to understand it more completely. It should be understood, however, that the invention is not limited solely to the particular examples given below.

EXAMPLE 1

N-[Furylmethyl-(3)]-nordesomorphine and its hydrochloride by method B

A suspension of 7.2 gm (0.03 mol) of nordesomorphine (dihydro-desoxynormorphine) in 210 ml of methanol was admixed with a solution of 7.5 gm of potassium carbonate in 12 ml of water, accompanied by vigorous stirring, and then 4.31 gm (0.033 mol) of furan-(3)-carboxylic acid chloride were added to the mixture over a period of 15 minutes. The reaction mixture was now stirred for 4 hours more, and thereafter the methanol was distilled off in vacuo, and the residue was shaken with a mixture of chloroform and water. The organic phase was separated, extracted with 2 N hydrochloric acid, washed twice with water, dried over sodium sulfate and evaporated in vacuo.

The residue, which consisted mainly of N-[-furoyl-(3)]-nordesomorphine and contained a small amount of N,O-di-[furoyl-(3)]-nordesomorphine, was dissolved in 200 ml of absolute tetrahydrofuran, and the resulting solution was added dropwise to a suspension of 2.3 gm (0.06 mol) of lithium aluminum hydride in 75 ml of absolute tetrahydrofuran, accompanied by stirring and cooling to maintain a temperature between 5° and 10°C. The reaction mixture was then refluxed for 1 hour, thereafter cooled on an ice bath and, while vigorously stirring, 4.5 ml of water were carefully added, and the mixture was admixed with 250 ml of a saturated aqueous diammonium tartrate solution and then stirred for 1 hour. Thereafter, the tetrahydrofuran (upper) phase was separated and evaporated. The aqueous phase was extracted three times with 50 ml of chloroform each, the evaporation residue of the tetrahydrofuran phase was dissolved in the combined chloroform extracts, and the resulting solution was washed with water, dried with sodium sulfate and evaporated in vacuo, yielding 6.8 gm (67.3% of theory) of the compound of the formula

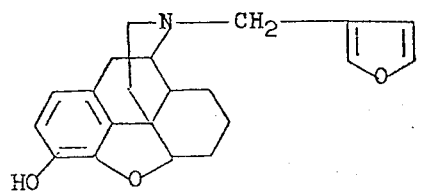

with a melting point of 165°–169°C. After recrystallization from ethyl acetate the pure base had a melting point of 169°–171°C.

Its hydrochloride monohydrate, obtained by acidifying the base with hydrochloric acid and crystallizing the salt from water, had a melting point of 190°–193°C.

EXAMPLE 2

N-[Furylmethyl-(3)]-Δ7-desoxy-normorphine and its hydrochloride by method A

A mixture consisting of 7.2 gm (0.028 mol) of Δ7-desoxy-normorphine, 3.54 gm (0.042 mol) of sodium bicarbonate, 3.6 gm (0.031 mol) of 3-chloromethyl-furan, 40 ml of tetrahydrofuran and 3 ml of dimethylformamide was refluxed for 3 hours. Thereafter, the reaction mixture was evaporated in vacuo, the residue was extracted with a mixture of chloroform and water, and the organic phase was separated, washed several times with water, dried over sodium sulfate and evaporated. The residue, raw N-[furylmethyl-(3)]-Δ7-desoxy-normorphine, was dissolved in a little methanol, the resulting solution was made just acid with methanolic hydrochloric acid, and the acidic solution was evaporated in vacuo. The residue was caused to crystallize by addition of acetone, and the crystalline product was recrystallized from methanol/ether, yielding 6 gm (57.2% of theory) of the hydrochloride of the formula

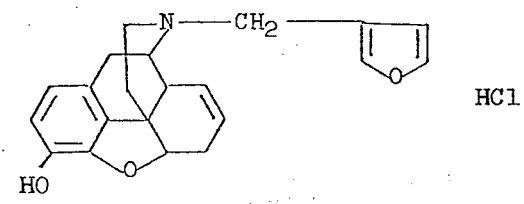

which had a melting point of 245°–247°C.

EXAMPLE 3

N-[Thienylmethyl-(3)]-dihydro-desoxynorcodeine and its maleate by method A

A mixture consisting of 9.2 gm (0.034 mol) of dihydro-desoxynorcodeine, 4.3 gm of sodium bicarbonate, 6.75 gm (0.038 mol) of 3-bromomethyl-thiophene, 50 ml of tetrahydrofuran and 25 ml of dimethylformamide was refluxed for 2 hours. Thereafter, the reaction mixture was evaporated in vacuo, the residue was shaken with a mixture of methylene chloride and water, and the methylene chloride phase was separated, washed several times with water, dried over sodium sulfate and evaporated. The residue, raw N-[thienylmethyl-(3)]-dihydro-desoxynorcodeine, was taken up in 2 N methanesulfonic acid and ether, and the aqueous phase was separated, made alkaline and extracted with methylene chloride. The organic extract was dried over sodium sulfate, and the solvent was evaporated in vacuo, leaving 9.2 gm (73.6% of theory) of the free base of the formula

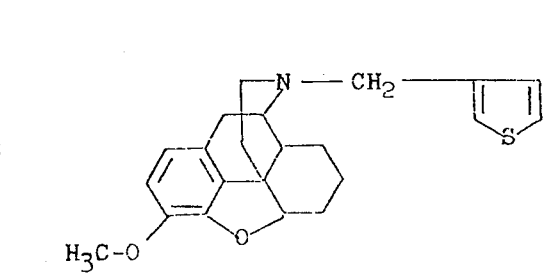

The free base was dissolved in methanol by addition of 3.25 gm of maleic acid, the solution was evaporated in vacuo, and the residue was recrystallized from water, yielding the maleate which had a melting point of 180°–182°C.

EXAMPLE 4

N-[Thienylmethyl-(3)]-nordesomorphine and its hydrochloride by method D

A mixture consisting of 3.6 gm (0.009 mol) of N-[thienylmethyl-(3)]-dihydrodesoxy-norcodeine hydrochloride and 17.5 gm of pyridine hydrochloride was heated for 30 minutes on an oil bath at 190°C. Thereafter, the resulting molten mixture was allowed to cool, was then dissolved in water, the resulting solution was admixed with 20 gm of sodium carbonate, and the pyridine was removed by steam distillation. The residue was then allowed to cool, was taken up in methylene chloride, and the resulting solution was dried with sodium sulfate and evaporated, yielding 1.9 gm (62% of theory) of N-[thienylmethyl-(3)]-nordesomorphine.

Its hydrochloride monohydrate, which decomposed above 190°C, was obtained by acidification of the base in conventional manner, and recrystallization of the salt first from ethanol/acetone and then from water.

EXAMPLE 5

N-[Thienylmethyl-(2)]-nordesomorphine and its hydrochloride by method F

A mixture consisting of 5.14 gm (0.02 mol) of nordesomorphine and 2.0 gm (0.04 mol) of 98% formic acid was stirred on an oil bath at 150°C until a homogeneous melt was formed, which required about 15 minutes. Thereafter, 2.5 gm (0.022 mol) of thiophene-2-aldehyde were added, and the mixture was refluxed for 30 minutes at 150°C, while stirring. After cooling, the resinous mass was treated with dilute methanesulfonic acid, and the acid solution was decanted from insoluble matter and then extracted with ether. The aqueous phase was treated with activated charcoal and filtered, and the filtrate was made alkaline with ammonia and then extracted with ether. The combined ether extracts were washed with water, dried over sodium sulfate and evaporated in vacuo, leaving 1.72 gm (24.2% of theory) of N-[thienylmethyl-(2)]-nordesomorphine.

The base was dissolved in acetone, the solution was admixed with methanolic hydrochloric acid until weakly acid reaction, and the crystals precipitated thereby were collected and recrystallized first from butanone/ethyl acetate and then from water in the presence of charcoal. The hydrochloride monohydrate thus obtained decomposed above 190°C.

EXAMPLE 6

N-[2-Methyl-furylmethyl-(3)]-O-acetyl-nordesomorphine of the formula

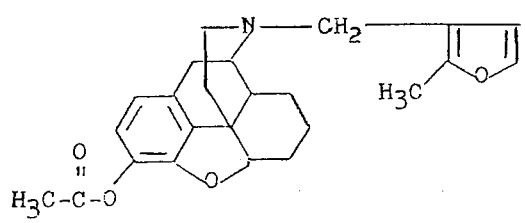

whose hydrochloride had a melting point of 135°–187°C, was obtained by reacting N-[2-methyl-furylmethyl-(3)]-nordesomorphine with acetic acid anhydride in pyridine (see method E).

EXAMPLE 7

Using a procedure analogous to that described in Example 3, N-[furylmethyl-(2)]-dihydrodesoxy-normorphine, m.p. 166°–167°C, was prepared from dihydrodesoxy-normorphine and 2-chloromethyl-furan.

EXAMPLE 8

Using a procedure analogous to that described in Example 3, N-[2-methyl-furylmethyl-(3)]-dihydrodesoxy-normorphine, m.p. 165°–167°C, was prepared from dihydrodesoxy-normorphine and 2-methyl-3-chloromethyl-furan.

EXAMPLE 9

Using a procedure analogous to that described in Example 6, N-[furylmethyl-(2)]-O-acetyl-dihydrodesoxy-normorphine maleate, m.p. 128°–131°C (decomp.), was prepared from N-[furylmethyl-(2)]-dihydrodesoxy-normorphine and acetic acid anhydride.

EXAMPLE 10

Using a procedure analogous to that described in Example 3, N-[furylmethyl-(2)]-dihydrodesoxy-norcodeine hydrochloride, m.p. 233°–235°C (decomp.), was prepared from dihydrodesoxy-norcodeine and 2-chloromethyl-furan.

EXAMPLE 11

Using a procedure analogous to that described in Example 3, N-[furylmethyl-(3)]-dihydrodesoxy-norcodeine hydrochloride, m.p. 225°–228°C, was prepared from dihydrodesoxy-norcodeine and 3-chloromethyl-furan.

EXAMPLE 12

Using a procedure analogous to that described in Example 1, N-[3-methyl-furylmethyl-(2)]-dihydrodesoxy-norcodeine hydrochloride, m.p. 220°–223°C, was prepared from dihydrodesoxy-norcodeine and 3-methyl-furan-2-carboxylic acid chloride.

EXAMPLE 13

Using a procedure analogous to that described in Example 3, N-[2-methyl-furylmethyl-(3)]-dihydrodesoxy-norcodeine hydrochloride, m.p. 207°–209°C (decomp.), was prepared from dihydrodesoxy-norcodeine and 2-methyl-3-chloromethylfuran.

EXAMPLE 14

Using a procedure analogous to that described in Example 1, N-[3-methyl-furylmethyl-(2)]-Δ7-desoxy-normorphine, m.p. 147°–149°C, was prepared from Δ7-desoxy-normorphine and 3-methyl-furan-2-carboxylic acid chloride.

EXAMPLE 15

Using a procedure analogous to that described in Example 2, N-[2-methyl-furylmethyl-(3)]-Δ7-desoxynormorphine hydrochloride, m.p. 240°–242°C (decomp.), was prepared from Δ7-desoxy-normorphine and 2-methyl-3-chloromethyl-furan.

EXAMPLE 16

Using a procedure analogous to that described in Example 2, N-[furylmethyl-(2)]-Δ7-desoxy-normorphine, m.p. 196°–198°C, was prepared from Δ7-desoxy-normorphine and 2-chloromethyl-furan.

EXAMPLE 17

Using a procedure analogous to that described in Example 2, N-[thienylmethyl-(2)]-Δ7-desoxy-normorphine hydrochloride . $C_2H_5OH$, m.p. 190°C, was prepared from Δ7-desoxy-normorphine and 2-bromomethyl-thiophene.

EXAMPLE 18

Using a procedure analogous to that described in Example 2, N-[furylmethyl-(2)]-Δ7-desoxy-norcodeine hydrochloride, m.p. 221°–223°C, was prepared from Δ7-desoxy-norcodeine and 2-chloromethyl-furan.

EXAMPLE 19

Using a procedure analogous to that described in Example 2, N-[furylmethyl-(3)]-Δ7-desoxy-norcodeine hydrochloride, m.p. 232°–234°C, was prepared from Δ7-desoxy-norcodeine and 3-chloromethyl-furan.

EXAMPLE 20

Using a procedure analogous to that described in Example 1, N-[3-methyl-furylmethyl-(2)]-Δ7-desoxy-norcodeine hydrochloride, m.p. 213°–214°C (decomp.), was prepared from Δ7-desoxy-norcodeine and 3-methyl-furan-2-carboxylic acid chloride.

EXAMPLE 21

N-[5-Methyl-furylmethyl-(2)]-Δ7-desoxy-norcodeine by method C

A solution of 2.3 gm (7.5 millimols) of Δ7-desoxy-norcodeine hydrochloride in 100 ml of aqueous 50% acetic acid was admixed with 0.83 gm of 30% formalin and 0.68 gm (8.3 millimols) of 5-methyl-furan, and the resulting mixture was stirred for 12 hours at room temperature. Thereafter, the reaction mixture was made alkaline with ammonia, was then extracted three times with 70 ml of chloroform each, and the combined organic extracts were dried over sodium sulfate and evaporated in vacuo. The residue, the raw desired reaction product, was purified by column-chromatography on aluminum oxide.

For this purpose, an as concentrated as possible solution of the raw product in chloroform was prepared, the solution was introduced into a chromatographic column charged with 40 gm of aluminum oxide (activity stage III, neutral), and the column was eluted with chloroform. The eluate fractions containing the pure product, as determined by thin-layer chromatographic testing, were combined and evaporated in vacuo, leaving 1.6 gm of the compound of the formula

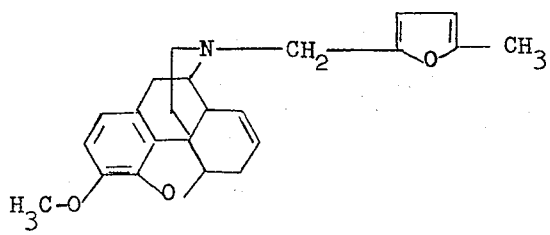

which had a melting point of 140°–141°C.

The compounds embraced by formula I above and their non-toxic, pharmacologically acceptable acid addition salts, have useful pharmacodynamic properties. More particularly, they exhibit opiate-antagonistic, especially morphine-antagonistic activities, as well as analgesic and antitussive activities in warm-blooded animals, such as mice and rats.

For pharmaceutical purposes the compounds of the formula I or a non-toxic acid addition salt thereof are administered to warm-blooded animals perorally, enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective analgesic and antitussive dosage unit of the compounds according to the present invention is from 0.166 to 5.0 mgm/kg body weight, preferably 0.83 to 2.5 mgm/kg body weight.

The following examples illustrate a few pharmaceutical dosage unit compositions comprising a compound of the formula I or a non-toxic, pharmacologically acceptable acid addition salt thereof as an active ingredient and represent the best mode contemplated of putting the invention into practical use. The parts are parts by weight unless otherwise specified.

EXAMPLE 22

Tablets

The tablet composition is compounded from the following ingredients:

| | |
|---|---|
| N-[Furylmethyl-(3)]-nordesomorphine hydrochloride | 50.0 parts |
| Lactose | 95.0 parts |
| Corn starch | 45.0 parts |
| Colloidal silicic acid | 2.0 parts |
| Soluble starch | 5.0 parts |
| Magnesium stearate | 3.0 parts |
| Total | 200.0 parts |

Preparation

The nordesomorphine compound is intimately admixed with the lactose and the corn starch, the mixture is moistened with an aqueous 10% solution of the soluble starch, the moist mass is forced through a 1 mm-mesh screen, the resulting granulate is dried at 40°C, the dry granulate is admixed with the colloidal silicic acid, and the composition is compressed into 200 mgm-tablets in a conventional tablet making machine. Each tablet contains 50 mgm of the nordesomorphine compound and is an oral dosage unit composition with effective opiate-antagonistic, analgesic and antitussive action.

EXAMPLE 23

Coated pills

The pill core composition is compounded from the following ingredients:

| | |
|---|---|
| N-[Thienylmethyl-(3)]-dihydrodesoxy-norcodeine maleate | 75.0 parts |
| Lactose | 100.0 parts |
| Corn starch | 65.0 parts |
| Colloidal silicic acid | 2.0 parts |
| Soluble starch | 5.0 parts |
| Magnesium stearate | 3.0 parts |
| Total | 250.0 parts |

11

Preparation

The ingredients are compounded in the same manner as in Example 22, and the composition is compressed into 250 mgm-pill cores which are subsequently coated with a thin shell consisting essentially of a mixture of sugar, talcum and gum arabic and finally polished with beeswax. Each coated pill contains 75 mgm of the norcodeine compound and is an oral dosage unit composition with effective opiate-antagonistic, analgesic and antitussive action.

EXAMPLE 24

Suppositories

The suppository composition is compounded from the following ingredients:

| | |
|---|---|
| N-Furfuryl-dihydrodesoxy-normorphine | 50.0 parts |
| Lactose | 250.0 parts |
| Suppository base (e.g. cocoa butter) | 1400.0 parts |
| Total | 1700.0 parts |

Preparation

The normorphine compound is intimately admixed with the lactose, and the mixture is blended with the aid of an immersion homogenizer into the suppository base which had previously been melted and cooled to about 40°C. 1700 mgm-portions of the composition are poured into cooled suppository molds and allowed to harden therein. Each suppository contains 50 mgm of the normorphine compound and is a rectal dosage unit composition with effective opiate-antagonistic, analgesic and antitussive action.

EXAMPLE 25

Hypodermic solution

The solution is compounded from the following ingredients:

| | |
|---|---|
| N-[Furylmethyl-(3)]-nordesomorphine hydrochloride | 50.0 parts |
| Sodium chloride | 5.0 parts |
| Double-distilled water   q.s.ad | 2000.0 parts by vol |

Preparation

The nordesomorphine compound and the sodium chloride are dissolved in the double-distilled water, the solution is filtered until free from suspended particles, and the filtrate is filled under aseptic conditions into 2 cc-ampules which are subsequently sterilized and sealed. Each ampule contains 50 mgm of the nordesomorphine compound, and its contents are an injectable dosage unit composition with effective opiate-antagonistic, analgesic and antussive action.

EXAMPLE 26

Drop solution

The solution is compounded from the following ingredients:

| | |
|---|---|
| N-(3-Methyl-furfuryl)-Δ7-desoxy-norcodeinehydrochloride | 0.70 parts |
| Methyl p-hydroxy-benzoate | 0.07 parts |
| Propyl p-hydroxy-benzoate | 0.03 parts |
| Demineralized water   q.s.ad | 100.0 parts by vol. |

Preparation

The norcodeine compound and the p-hydroxy-benzoates are dissolved in the demineralized water, the solution is filtered, and the filtrate is filled into 100 ml-bottles. 10 ml of the solution contain 70 mgm of the norcodeine compound and are an oral dosage unit composition with effective opiate-antagonistic, analgesic and antitussive action.

Analogous results are obtained when any one of the other compounds embraced by formula I or a non-toxic acid addition salt thereof is substituted for the particular normorphine or norcodeine derivative in Examples 22 through 26. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition consisting essentially of an inert pharmaceutical carrier and an effective opiate-antagonistic, analgesic or antitussive amount of a compound of the formula

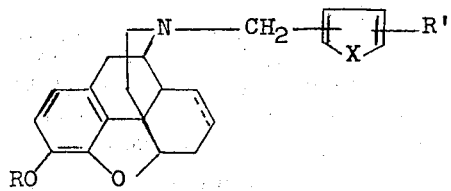

wherein

R is hydrogen, methyl or acetyl,
R' is hydrogen or methyl, and
X is oxygen or sulfur, or a non-toxic, pharmacologically acceptable acid addition salt thereof.

2. A composition of claim 1,
where
R is hydrogen,
R' is hydrogen or methyl, and
X is oxygen or sulfur.

3. A composition of claim 1, where said compound is N-[furylmethyl-(3)]-nordesomorphine or a non-toxic, pharmacologically acceptable acid addition salt thereof.

4. A composition of claim 1, where said compound is N-[thienylmethyl-(3)]-dihydrodesoxy-norcodeine or a non-toxic, pharmacologically acceptable acid addition salt thereof.

5. A composition of claim 1, where said compound is N-furfuryl-dihydroxydesoxy-normorphine or a non-toxic, pharmacologically acceptable acid addition salt thereof.

6. A composition of claim 1, where said compound is N-(3-methyl-furfuryl)-Δ7-desoxy-norcodeine or a non-toxic, pharmacologically acceptable acid addition salt therof.

7. The method of antagonizing the pharmacological effects of an opiate, raising the pain threshold or supressing the cough reflex in a warm-blooded animal, which comprises administering to said animal an effective opiate-antagonistic, analgesic or antitussive amount of a compound of the formula

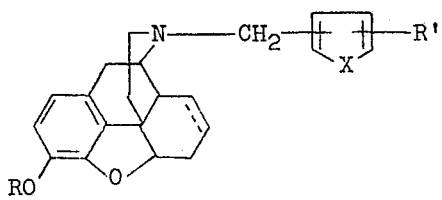

wherein
R is hydrogen, methyl or acetyl,
R' is hydrogen or methyl, and
X is oxygen or sulfur,
or a non-toxic, pharmacologically acceptable acid addition salt thereof.

8. The method of claim 7, where
R is hydrogen
R' is hydrogen or methyl, and
X is oxygen or sulfur.

9. The method of claim 7, where said compound is N-[furylmethyl-(3)]-nordesomorphine or a non-toxic, pharmacologically acceptable acid addition salt thereof.

10. The method of claim 7, where said compound is N-[thienylmethyl-(3)]-dihydrodesoxy-norcodeine or a non-toxic, pharmacologically acceptable acid addition salt thereof.

11. The method of claim 7, where said compound is N-furfuryl-dihydroxydesoxy-normorphine or a non-toxic, pharmacologically acceptable acid addition salt thereof.

12. The method of claim 7, where said compound is N-(3-methyl-furfuryl)-$\Delta$7-desoxy-norcodeine or a non-toxic, pharmacologically acceptable acid addition salt thereof.

* * * * *